US012733852B2

(12) United States Patent
Hong et al.

(10) Patent No.: US 12,733,852 B2
(45) Date of Patent: Sep. 15, 2026

(54) METHOD AND APPARATUS FOR ANALYZING EYE MOVEMENT

(71) Applicants: Industry Academic Cooperation Foundation, Hallym University, Chuncheon-Si (KR); NEUROEARS CO., LTD., Anyang-Si (KR)

(72) Inventors: Sung Kwang Hong, Seongnam-si (KR); Eun-Cheon Lim, Anyang-Si (KR); Changje Cho, Anyang-Si (KR)

(73) Assignees: Industry Academic Cooperation Foundation, Hallym University, Chuncheo-Si (KR); Neuroears Co., Ltd., Anyang-Si (KR)

( * ) Notice: Subject to any disclaimer, the term of this patent is extended or adjusted under 35 U.S.C. 154(b) by 360 days.

(21) Appl. No.: 18/508,883

(22) Filed: Nov. 14, 2023

(65) Prior Publication Data

US 2024/0197218 A1 Jun. 20, 2024

(30) Foreign Application Priority Data

Dec. 19, 2022 (KR) ........................ 10-2022-0178487

(51) Int. Cl.
*A61B 5/16* (2006.01)
*A61B 5/00* (2006.01)
(Continued)

(52) U.S. Cl.
CPC ............ *A61B 5/163* (2017.08); *A61B 5/7275* (2013.01); *A61B 5/7405* (2013.01);
(Continued)

(58) Field of Classification Search
CPC ..... A61B 5/163; A61B 5/7275; A61B 5/7405; A61B 5/1103; A61B 5/1128;
(Continued)

(56) References Cited

U.S. PATENT DOCUMENTS 8,708,884 B1 * 4/2014 Smyth .................. A61M 21/00 706/15
2004/0003409 A1 * 1/2004 Berstis ............... H04N 21/2187 348/E7.086
(Continued)

FOREIGN PATENT DOCUMENTS

KR 20160061691 A 6/2016
KR 20200027210 A 3/2020
(Continued)

OTHER PUBLICATIONS

Office Action issued in Korean Application No. 10-2022-0178487; Dated Apr. 11, 2025 (10 pages).

*Primary Examiner* — Mohammed A Hasan
(74) *Attorney, Agent, or Firm* — Osha Bergman Watanabe & Burton LLP

(57) ABSTRACT

The present disclosure relates to an eye movement analysis method performed in an eye movement analysis apparatus, the eye movement analysis method including: receiving a facial image; obtaining an eye image that corresponds to a part of an eye that determines a midpoint position of the eye in the facial image; analyzing movement of the eye based on movement of the midpoint position in the facial image; and visually displaying a direction of the movement of the eye.

10 Claims, 3 Drawing Sheets

(51) Int. Cl.
*G06T 7/00* (2017.01)
*G06T 7/11* (2017.01)

(52) U.S. Cl.
CPC .............. *G06T 7/0012* (2013.01); *G06T 7/11* (2017.01); *G06T 2207/20084* (2013.01); *G06T 2207/30041* (2013.01)

(58) Field of Classification Search
CPC ... A61B 5/4023; A61B 5/4064; A61B 5/4863; A61B 5/746; A61B 5/7264; A61B 5/0013; A61B 5/742; G06T 7/0012; G06T 7/11; G06T 2207/20084; G06T 2207/30041; G06T 7/246; G16H 30/40; G16H 50/20
USPC .......................................................... 351/209
See application file for complete search history.

(56) References Cited

U.S. PATENT DOCUMENTS

2009/0164132 A1* 6/2009 Jung .................... A61B 5/0533 600/407
2019/0089701 A1* 3/2019 Mercury .............. G06Q 10/105
2022/0087524 A1* 3/2022 Sasaki .................... A61B 5/163
2022/0117529 A1* 4/2022 Filimonov ............... A61B 5/18

FOREIGN PATENT DOCUMENTS

KR 20200051632 A 5/2020
KR 20200089204 A 7/2020
KR 20210123949 A 10/2021

* cited by examiner

[FIG. 1]
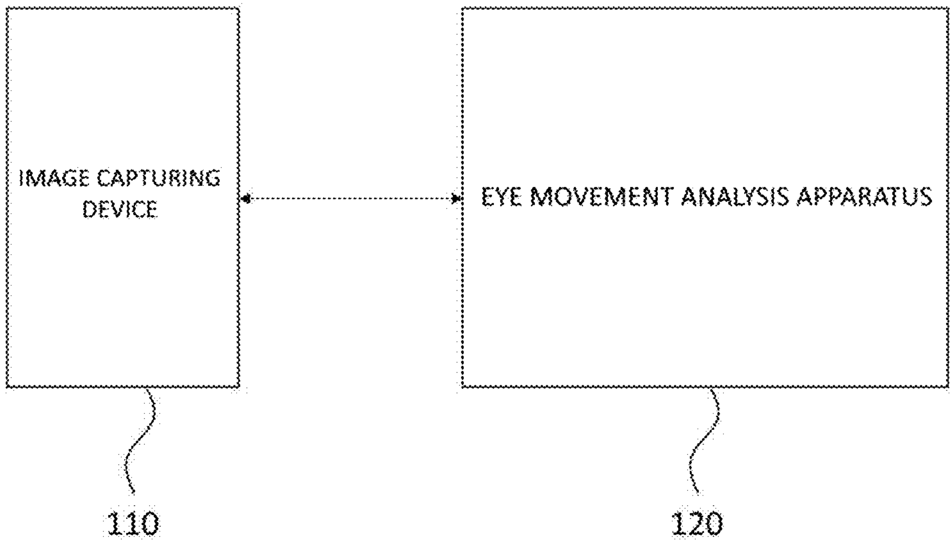
[FIG. 2]
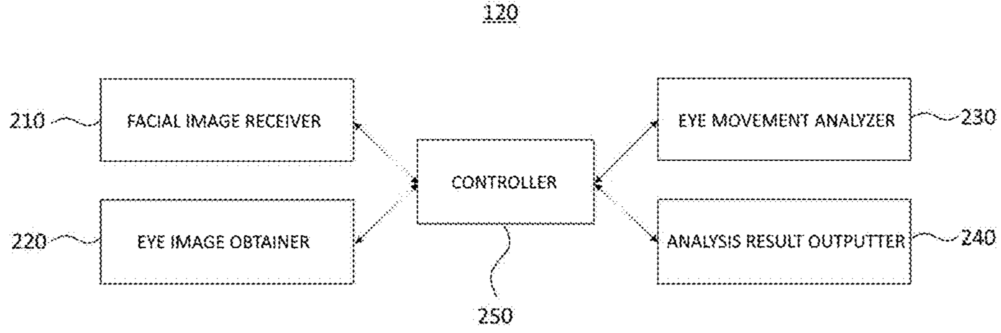

[FIG. 3]
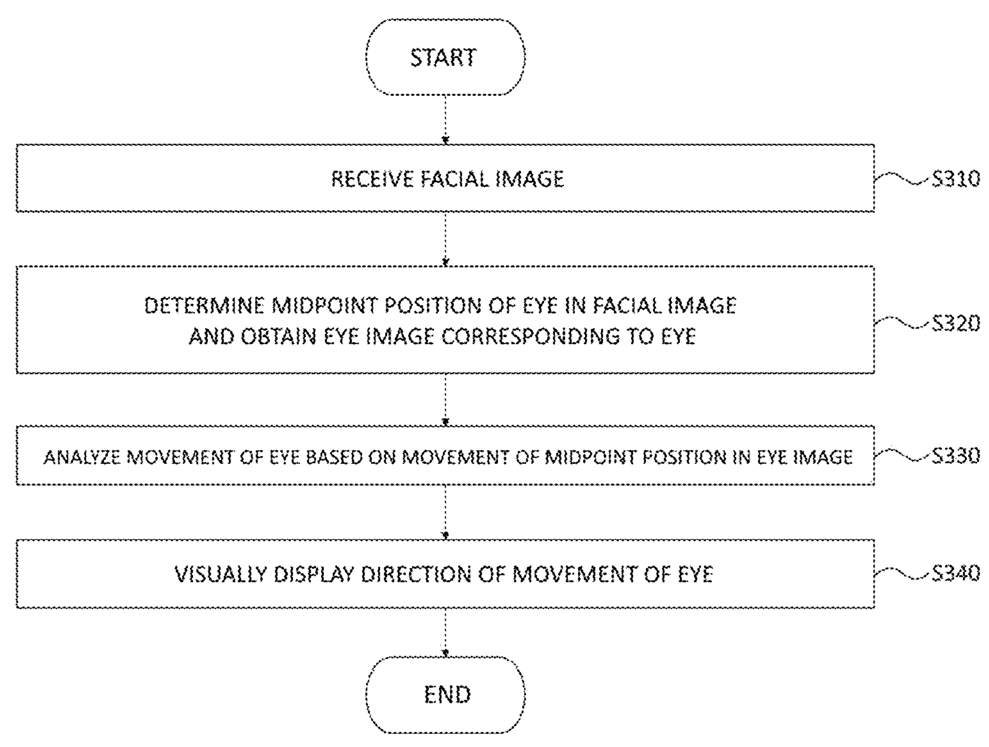
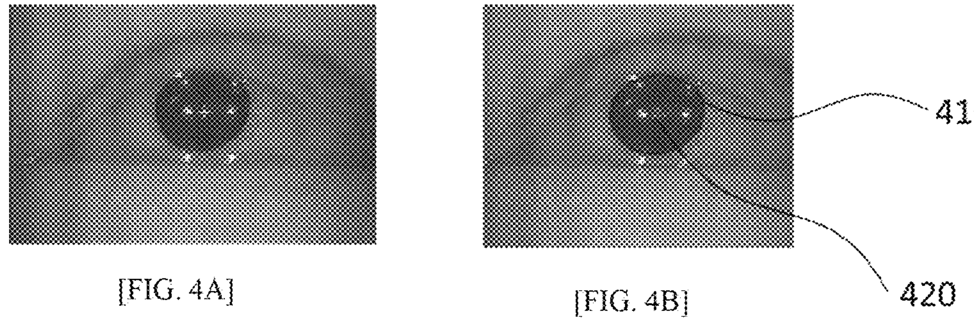
[FIG. 4A] [FIG. 4B]

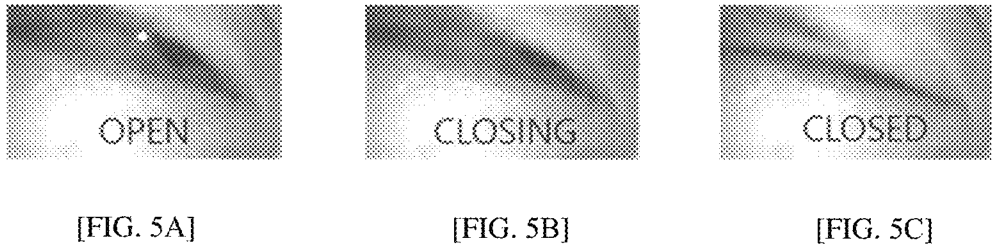
[FIG. 5A] [FIG. 5B] [FIG. 5C]
[FIG. 6]
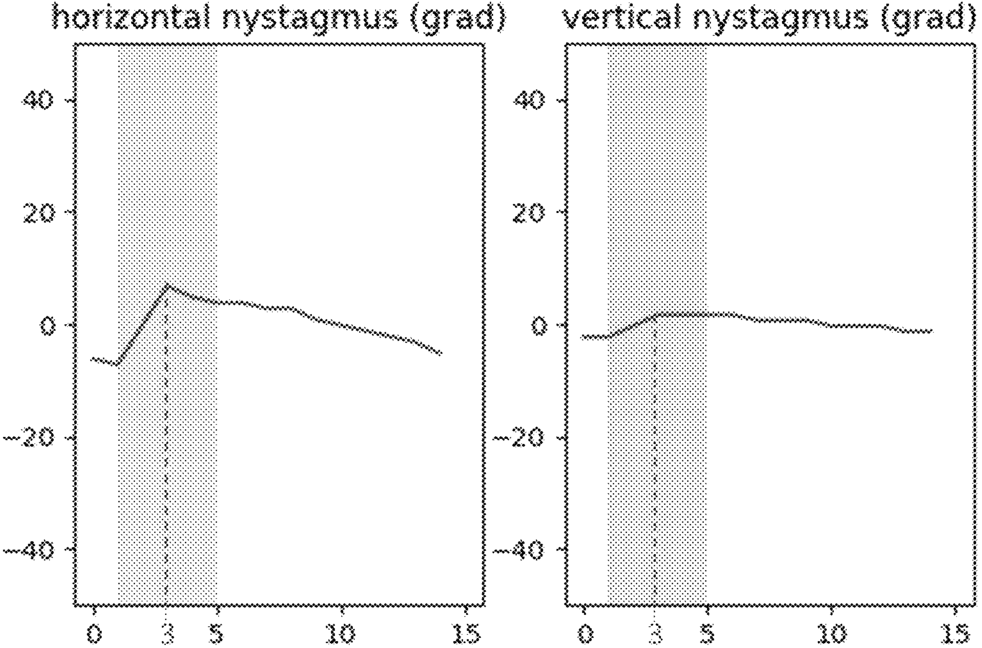
[FIG. 7]
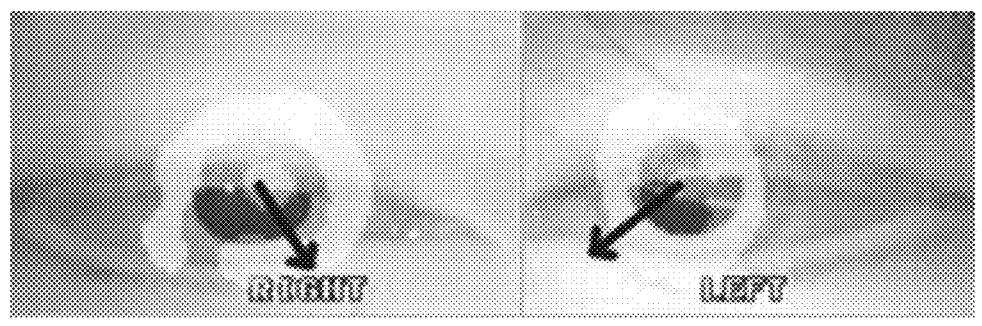

METHOD AND APPARATUS FOR ANALYZING EYE MOVEMENT

CROSS-REFERENCE TO RELATED APPLICATION

This application claims priority to and the benefit of Korean Patent Application No. 2022-0178487, filed on Dec. 19, 2022, the disclosure of which is incorporated herein by reference in its entirety.

BACKGROUND

1. Field of the Invention

The present disclosure relates to an eye movement analysis technology, and more particularly, to a method and apparatus for analyzing eye movement that can observe and analyze eye movement from a remote place without exposure of the face of a patient.

2. Discussion of Related Art

Dizziness, which is one main neurotological condition, can be diagnosed through observation of eye movement, particularly, eye movement that corresponds to a change in a head position. That is, measurement of the vestibulo-ocular reflex is one key examination process that must be performed for a patient with dizziness. Nowadays, a metaverse is implemented while a virtual reality device is worn, and a gyro sensor for sensing movement of the head position, an eye tracker for measuring eye movement, and the like are attached to the virtual reality device. Thus, diagnosis of dizziness has a characteristic that the process for diagnosis of dizziness in the metaverse is the closest to reality compared to processes for diagnosis of any other medical conditions. Also, even in terms of treatment, a treatment plan for dizziness is established by tracking eye movement and a change in the head position, and thus utilization of a metaverse platform is expected to be possible for treating dizziness.

In recent years, various methods have also been introduced in the field of telemedicine, and telemedicine is now utilized in various clinical fields abroad. Forms of telemedicine used so far for dizziness in the field of neurotology include an eye movement test conducted by a non-professional, after which a professional watches a video of the test and eye movement from a remote place and provides a diagnosis. However, due to characteristics of the test in which the patient's face is inevitably exposed as it is, and the eye movement is indirectly observed instead of being directly observed, there may be an information security issue or various diagnostic difficulties. Also, patients who complain of dizziness do not complain of dizziness all the time and often do not have dizziness at the time of visit to the hospital, and thus measurement of eye movement at the time of dizziness is the most important for diagnosis of dizziness. However, except for a method of self-measuring and saving eye movement at the time of dizziness using a video camera or the like and loading the self-measured eye movement, there is no other method for measuring and checking eye movement at the time of dizziness.

Also, eye movement is directly observed by the naked eye or tested by utilizing a medical device referred to as a nystagmograph. When the vestibular function is reduced, abnormal vestibulo-ocular reflex is exhibited, and eye movement that occurs in this case is referred to as nystagmus. Nystagmus consists of a slow component and a quick component. For example, when the right vestibular function is reduced, a slow, rightward eye movement is exhibited first, and then a quick, corrective movement is exhibited leftward. In this case, since the slow eye movement is not easy to see and the quick eye movement is easier to see, it can be seen that the patient's eye quickly moves to the opposite side of the lesion, that is, the left side. Other than the eye movement consisting of a slow component and a quick component, eye movement consists of only the slow component or the quick component in some cases. Since such cases often imply a problem in the central nervous system, it is important to distinguish a problem in the central nervous system from abnormal eye movement.

In order to observe eye movement, a nystagmograph enlarges the shape of an eye and imparts a dark room effect to prevent an eye from gazing at a specific fixed point and strengthen the eye movement. Thus, the nystagmograph has an advantage that it can more accurately observe eye movement than the naked eye. However, a large amount of training is necessary to observe and diagnose nystagmus using a nystagmograph. Also, when direct observation of eye movement is impossible, eye movement is shown by a graph, but when a patient is blinking or closing the eye, the eye movement is not properly shown by a graph, and there is an inconvenience that a tester should continuously make sure that the patient keeps the eye open.

RELATED ART DOCUMENT

Patent Document (Patent Document 1) Korean Patent Publication No. 10-2020-0027210

SUMMARY OF THE INVENTION

The present disclosure is directed to providing a method and apparatus for analyzing eye movement that can observe and analyze eye movement from a remote place without direct exposure of the face of a patient.

The present disclosure is also directed to providing a method and apparatus for analyzing eye movement that can interpret eye movement, which can be utilized as an aid to diagnosis, through an algorithm learned by deep learning and provide an arrow indicating a direction of the eye movement.

The present disclosure is also directed to providing a method and apparatus for analyzing eye movement that can automatically exclude a measured value from analysis when a decrease in accuracy of eye movement measurement occurs and provide auditory feedback to allow a patient to focus on the test.

Objectives to be achieved by the present disclosure are not limited to those mentioned above, and other unmentioned objectives should be clearly understood by those of ordinary skill in the art from the description below.

A first aspect of the present disclosure provides an eye movement analysis method performed in an eye movement analysis apparatus, the eye movement analysis method including: (a) receiving a facial image; (b) determining a midpoint position of an eye in the facial image and obtaining an eye image that corresponds to the eye; (c) analyzing movement of the eye based on movement of the midpoint position in the facial image; and (d) visually displaying a direction of the movement of the eye.

Step (b) may include: detecting a pupil object through image segmentation in the facial image; and searching for the midpoint position of the eye by calculating a central moment of the pupil object based on the detected pupil object.

Step (c) may include: detecting blinking of the eye in the facial image using an artificial intelligence model and classifying the blinking of the eye into an open state, a closing state, and a closed state; extracting images classified as the open state and the closing state, among the classifications of the blinking of the eye, from the facial image; predicting a midpoint position of the closing state, among the classifications of the blinking of the eye, in the facial image by restoring a part of the eye that is covered by an eyelid; and interpolating a midpoint position of the closed state, among the classifications of the blinking of the eye, in the facial image based on a midpoint position of the closing state prior to the closed state and a midpoint position of the open state after the closed state.

Step (d) may include providing an auditory alarm to a testee in a case in which the closed state continues for a certain amount of time or more in the facial image.

Step (c) may include: detecting an eye movement consisting of a slow component and a quick component among vertical, horizontal, and rotary movements of the eye from the extracted image; and detecting an eye movement consisting of only the slow component or an eye movement consisting of only the quick component among the vertical, horizontal, and rotary movements of the eye from the extracted image, wherein the rotary movement may be defined as a movement in which the vertical and horizontal movements of the eye simultaneously occur in the extracted image.

Step (d) may include, in a case in which the eye movement consisting of only the slow component or the eye movement consisting of only the quick component is detected, providing a visual alarm to a tester.

Step (c) may include: selecting a frame with a peak value at which a size of a change amount of the vertical or horizontal movement of the eye per unit time in the extracted image is the largest as a key frame; setting a speed of the slow component based on the selected key frame; and determining a component as the quick component in a case in which a speed of the component is a threshold value or more based on the speed of the slow component and determining a component as the slow component in a case in which a speed of the component is less than the threshold value.

The eye movement analysis method may further include: in a case in which a speed of one of the vertical and horizontal movements of the eye per unit time in the extracted image is less than the threshold value and a speed of the other movement is the threshold value or more, determining a direction of the vertical or horizontal movement having the speed that is the threshold value or more as a movement direction; and in a case in which speeds of the vertical and horizontal movements of the eye per unit time in the extracted image are the threshold value or more, determining the movement of the eye as the rotary movement and determining the horizontal direction as a rotation direction.

The eye movement analysis method may further include: selecting a frame with a peak value at which a size of a change amount of a movement of the eye per unit time in the extracted image is the largest as a key frame; and determining a direction of the eye that is observed from the selected key frame as a direction of an arrow.

Step (d) may include: providing, together with an eye movement direction indicating that the eye movement corresponds to the vertical, horizontal, or rotary movement, a direction of an arrow that corresponds to a direction of the quick component among the components of the eye movement; and expressing the eye movement as an animation.

A second aspect of the present disclosure provides an eye movement analysis apparatus including: a facial image receiver configured to receive a facial image; an eye image obtainer configured to obtain an eye image that corresponds to a part of an eye that determines a midpoint position of the eye in the facial image; an eye movement analyzer configured to analyze movement of the eye based on movement of the midpoint position in the eye image; and an analysis result outputter configured to visually display a direction of the movement of the eye.

A third aspect of the present disclosure provides a computer program stored in a computer-readable medium, wherein, in a case in which a command of the computer program is executed, the eye movement analysis method is performed.

BRIEF DESCRIPTION OF THE DRAWINGS

The above and other objects, features and advantages of the present disclosure will become more apparent to those of ordinary skill in the art by describing exemplary embodiments thereof in detail with reference to the accompanying drawings, in which:

FIG. 1 is a block diagram of an eye movement analysis system according to an exemplary embodiment of the present disclosure.

FIG. 2 is a block diagram illustrating an eye movement analysis apparatus according to one embodiment.

FIG. 3 is a flowchart illustrating an eye movement analysis method according to one embodiment.

FIGS. 4A, 4B, 5A, 5B, 5C, 6 and 7 are exemplary views for describing the eye movement analysis method according to one embodiment.

DETAILED DESCRIPTION OF EXEMPLARY EMBODIMENTS

Hereinafter, advantages and features of the present disclosure and methods of achieving the same will become apparent from the embodiments described in detail below with reference to the accompanying drawings. However, the present disclosure is not limited to the embodiments disclosed below and may be implemented in various different forms. The embodiments herein are provided to make the disclosure complete and to completely inform those of ordinary skill in the art to which the present disclosure pertains of the scope of the disclosure, and the present disclosure is defined only by the scope of claims. Throughout the specification, like reference numerals refer to like components. The term “and/or” includes each of mentioned items and all combinations of one or more of the items.

Terms such as “first” and “second” are used to describe various elements, components, and/or sections, but, of course, the elements, components, and/or sections are not limited by the terms. The terms are only used to distinguish one element, component, or section from another element, component, or section. Therefore, of course, a first element, first component, or first section mentioned below may also be a second element, second component, or second section within the technical spirit of the present disclosure.

Also, identification codes (for example, a, b, c, and the like) indicating each step are used for convenience of description and do not describe an order of the steps. The steps may be performed in an order different from a stated order unless a specific order is clearly described in the context. That is, the steps may be performed in an order identical to a stated order, may be performed substantially simultaneously, or may be performed in the opposite order.

Terms used herein are for describing the embodiments and are not intended to limit the present disclosure. In the specification, a singular expression includes a plural expression unless the context clearly indicates otherwise. "Comprises" and/or "comprising" used herein do not exclude the possibility of the presence or addition of one or more components, steps, operations, and/or elements other than those mentioned.

Unless otherwise defined, all terms including technical or scientific terms used herein have the same meaning as commonly understood by one of ordinary skill in the art to which the present disclosure pertains. Terms, such as those defined in commonly used dictionaries, should not to be construed in an idealized or overly formal sense unless expressly so defined herein.

Also, in describing embodiments of the present disclosure, when detailed description of a known function or configuration is determined as having the possibility of unnecessarily obscuring the gist of the present disclosure, the detailed description thereof will be omitted. Also, terms used below are terms defined in consideration of functions in the present disclosure and may vary according to an intention or customary practice of a user or an operator. Therefore, the terms should be defined based on the content throughout the specification.

FIG. 1 is a block diagram of an eye movement analysis system according to an exemplary embodiment of the present disclosure.

Referring to FIG. 1, an eye movement analysis system 100 includes an image capturing device 110 and an eye movement analysis apparatus 120, and the image capturing device 110 and the eye movement analysis apparatus 120 may be connected through a network and transmit and receive data to and from each other.

The image capturing device 110 is a device for capturing a facial image of a testee. The image capturing device 110 may be a device that is carried by the testee and can self-capture a facial image of the testee including an eye area of the testee any time the testee experiences dizziness. For example, the image capturing device 110 may be a mobile phone or smartphone including a camera, and various types of devices may be used as the image capturing device 110 as long as the device includes a camera that can self-capture an image.

The eye movement analysis apparatus 120 is an apparatus for performing an eye movement analysis method according to the present disclosure and analyzes eye movement from the facial image received from the image capturing device 110 and provides an analysis result to a tester for the analysis result to be used in diagnosis. The eye movement analysis apparatus 120 may be a computer, may run an application or program installed therein to perform the eye movement analysis method, and may include a user interface so that the input and output of data is controlled. Here, the computer may be understood as any type of hardware apparatus including at least one processor or, according to embodiments, may be understood to have a meaning that also encompasses a software configuration that operates in the corresponding hardware apparatus. For example, the computer may be understood to have a meaning that encompasses all of a smartphone, a tablet personal computer (PC), a desktop, a laptop, and user clients and applications run on each of the devices, but is not limited thereto.

The eye movement analysis system may be utilized in a digital twin or a metaverse. That is, when a facial image of a testee is captured through the image capturing device 110 and sent to the eye movement analysis apparatus 120, the eye movement analysis apparatus 120 may extract only the eye movement from the facial image and identically express the eye movement as eye movement of a virtual avatar in a metaverse and may allow a tester to observe the eye movement of the avatar and diagnose dizziness of the testee. In this case, since the virtual avatar is used, the testee's face is not directly exposed, and thus a problem of information leakage or security may be more efficiently addressed. The eye movement analysis method performed through the eye movement analysis apparatus 120 may be applied to a digital twin or a metaverse, but the following description will be given without limiting the application field.

In one embodiment, although not illustrated in FIG. 1, the eye movement analysis system 100 may include a tester terminal, and the tester terminal may be connected to the eye movement analysis apparatus 120 and may receive an analysis result from the eye movement analysis apparatus 120, output the analysis result, receive feedback on the analysis result from a tester, and send the feedback to the eye movement analysis apparatus 120.

FIG. 2 is a block diagram illustrating the eye movement analysis apparatus according to an exemplary embodiment.

Referring to FIG. 2, the eye movement analysis apparatus 120 includes a facial image receiver 210, an eye image obtainer 220, an eye movement analyzer 230, an analysis result outputter 240, and a controller 250. Here, the controller 250 controls operations and data flows of the facial image receiver 210, the eye image obtainer 220, the eye movement analyzer 230, and the analysis result outputter 240.

The facial image receiver 210 receives a facial image captured by the image capturing device 110. The facial image receiver 210 may receive a captured facial image from the image capturing device 110 in real time.

The eye image obtainer 220 obtains only an image that corresponds to an eye from the facial image received by the facial image receiver 210. That is, the eye image obtainer 220 obtains only the image relating to the eye for which it is necessary to analyze eye movement, without exposure of the testee's face.

The eye movement analyzer 230 analyzes movement of the eye in the eye image obtained by the eye image obtainer 220 and analyzes whether the movement of the eye corresponds to a slow component or a quick component and whether a direction of the movement is vertical, horizontal, or rotary.

The analysis result outputter 240 outputs an eye movement analysis result. The analysis result outputter 240 may display a direction of eye movement to assist in diagnosis by the tester, and in a case in which eye movement is abnormal or is unable to be analyzed, the analysis result outputter 240 may provide a corresponding alarm to the tester or testee to increase accuracy of eye movement analysis.

Operations performed by each component of the eye movement analysis apparatus 120 illustrated in FIG. 2 will be described in detail below with reference to FIG. 3. Steps to be described with reference to FIG. 3 are described as being performed by different components, but the present disclosure is not limited thereto, and according to embodiments, at least some of the steps may be performed by components identical to or different from each other.

FIG. 3 is a flowchart illustrating an eye movement analysis method according to one embodiment.

Referring to FIG. 3, the facial image receiver 210 receives a facial image (step S310). The facial image receiver 210 may receive a facial image from the image capturing device 110 in real time, and the facial image corresponds to an image including the testee's face including an eye of the testee.

The eye image obtainer 220 determines a midpoint position of the eye in the facial image and obtains an eye image corresponding to the eye (step S320). The eye image obtainer 220 may detect a pupil object through image segmentation from the facial image and may search for the midpoint position of the eye based on the detected pupil object. More specifically, the eye image obtainer 220 obtains an eye image corresponding to only the eye by identifying a pupil area through an object segmentation artificial intelligence model for the darkest part in an eye image frame of the facial image and calculating a central moment of the pupil area to determine the midpoint position of the eye. For example, referring to FIG. 4, the eye image obtainer 220 may identify a pupil object 410 through segmentation of an eye area in an eye image frame shown in FIG. 4A and may calculate a central moment of the pupil to search for a midpoint position 420 of the eye.

The eye movement analyzer 230 analyzes movement of the eye based on movement of the midpoint position in the eye image (step S330), and the analysis result outputter 240 visually displays a direction of the movement of the eye (step S340). The eye movement analyzer 230 may perform prediction by applying an artificial intelligence model for a vector that indicates a gaze direction starting from the midpoint position and may track a direction of the movement of the eye based on a result of the performed prediction.

First, the eye movement analyzer 230 may detect blinking of the eye from the eye image using an artificial intelligence model and may classify the blinking of the eye into an open state, a closing state, and a closed state. The eye movement analyzer 230 analyzes movement of the eye by extracting only the images classified as the open state and the closing state, among the classifications of the blinking of the eye, from the eye image. For example, as illustrated in FIG. 5, the eye movement analyzer 230 may classify states of the eye into the open state, the closing state, and the closed state and may extract images classified as the open state and the closing state, from which eye movement analysis is possible, to analyze movement of the eye. The eye movement analyzer 230 may apply an artificial intelligence model and, for the closing state, restore a part of the eye that is covered by an eyelid to predict a midpoint position in a case in which the part of the eye is not covered by the eyelid and, for the closed state, interpolate a midpoint position of the closed state based on a midpoint position of the closing state prior to the closed state and a midpoint position of the open state after the closed state. In this way, the eye movement analyzer 230 may analyze eye movement.

In one embodiment, when the eye movement analyzer 230 detects that the closed state among the classifications of the blinking of the eye is continuing for a certain amount of time or more, the analysis result outputter 240 may provide an auditory alarm to the testee. The analysis result outputter 240 may provide, to the image capturing device 110, an auditory alarm to make sure the testee keeps the eye open for eye movement analysis. Here, the image capturing device 110 may include a speaker function, and in a case in which a speaker device is connected to the eye movement analysis apparatus 120, separately from the image capturing device 110, the analysis result outputter 240 may send an auditory alarm to the separate speaker device. For example, in a case in which the testee captures his or her facial image using a smartphone and provides the captured facial image to the eye movement analysis apparatus 120, an auditory alarm may be sent to the smartphone, and in a case in which the testee captures his or her facial image using a separate camera while wearing a headset or earphones and provides the captured facial image to the eye movement analysis apparatus 120, an auditory alarm may be sent to the headset or earphones.

The eye movement analyzer 230 may, from images extracted after being classified as the open state and the closing state among the classifications of the blinking of the eye, detect vertical, horizontal, or rotary movement, which is two-axis movement, of the eye and detect eye movement consisting of a slow component and a quick component from the detected movement. Here, eye movement in which the two components that correspond to the slow component and the quick component are simultaneously present is referred to as nystagmus, and nystagmus is a symptom that may occur when there is a disorder of the central nervous system such as cochlear hypofunction or cerebellar infarction.

First, the eye movement analyzer 230 may detect a movement in which the vertical and horizontal movements of the eye are simultaneously observed in the extracted image as a rotary movement. More specifically, the eye movement analyzer 230 may determine an eye movement as the rotary movement in a case in which speeds of the vertical and horizontal movements of the eye per unit time in the extracted image are a preset threshold value or more. When an ocular muscle moves the eye with a centrifugal force, since the eye is not able to move by specific torque or more in one direction to a certain extent or more, the movement in which the vertical and horizontal movements are simultaneously present may be defined as the rotary movement.

More specifically, in a method of detecting a slow component and a quick component, the eye movement analyzer 230 selects a frame with a peak value at which a size of a change amount of the vertical or horizontal movement of the eye per unit time in the extracted image is the largest as a key frame and sets a speed of the slow component based on the selected key frame. Then, the eye movement analyzer 230 determines a component as the quick component in a case in which a speed of the component is a threshold value or more based on the speed of the slow component and determines a component as the slow component in a case in which a speed of the component is less than the threshold value. For example, the eye movement analyzer 230 may calculate, for each frame, gradient (that is, movement speed) values of vertical and horizontal movement values of a midpoint position within 0.5 seconds (for example, frames within 15 frames based on a 30 FPS video) to measure vertical and horizontal movements at the midpoint position of the pupil, calculate a movement average value thereof, and then select a position of the largest movement value within the most recent 0.5 seconds as a key frame. Referring to FIG. 6, since a movement average value of horizontal and vertical gradient values is indicated and the horizontal and vertical gradient values are the largest in frame #3 in the entire window (the most recent 15 frames), frame #3 may be selected as a key frame. Here, when a movement speed value is a positive number in the key frame based on a starting point (frame #0), a rightward movement may be defined horizontally and an upward movement may be defined vertically, and when a movement speed value is a negative number, a leftward movement may be defined horizontally and a downward movement may be defined vertically, and this may be applied in the opposite way according to a calculation method. Also, when the key frame is selected, the eye movement analyzer 230 may set the speed of the slow component based on the key frame and may determine a component as the quick component when the speed of the component is a threshold value or more based on the speed of the slow component and determine a component as the slow component when the speed of the component is less than the threshold value. Here, the threshold value may be set by a tester.

The eye movement analyzer 230 may, from vertical, horizontal, and rotary movements, which are two-axis movements, of the eye in the extracted image, detect an eye movement consisting of only the slow component or an eye movement consisting of only the quick component. Here, the slow component and the quick component may be determined in the same manner as above, and an eye movement consisting of only the slow component or the quick component is a symptom that occurs in the presence of a brain disease.

In one embodiment, when an eye movement consisting of only the slow component or an eye movement consisting of only the quick component is detected by the eye movement analyzer 230, since the detection may imply a problem in the central nervous system such as a brain disease, instead of a normal vestibulo-ocular reflex, the analysis result outputter 240 may provide a visual alarm to the tester. That is, on a screen viewed by the tester, the analysis result outputter 240 may output a guide message indicating that an eye movement consists of only the slow component or the quick component or output a message indicating that an additional test (for example, a magnetic resonance imaging (MRI) test) is necessary.

In one embodiment, when a movement value per unit time of vertical, horizontal, or rotary movement is less than a preset threshold value in a frame of a certain size around the key frame for movement measurement, and it is determined that a slow component and a quick component are not present in the eye movement, the eye movement analyzer 230 may distinguish the corresponding frame as data to be excluded from analysis. When the size of eye movement per unit time does not exceed a certain numerical value, a gradient value is smoothened and is not selected within a window in the process of calculating a movement average value. This is a case in which a slow component and a quick component are not present, and since the testee is normal in this case, the data is not significant in predicting a direction of a lesion of a testee with a problem in the central nervous system or the peripheral nervous system and thus is excluded from analysis.

The eye movement analyzer 230 may, for an eye movement consisting of a slow component and a quick component, determine a direction of the eye movement by augmentation. In a case in which a speed of one of the vertical and horizontal movements of the eye per unit time in the extracted image is less than a threshold value and a speed of the other movement is the threshold value or more, the eye movement analyzer 230 may determine a direction of the vertical or horizontal movement having the speed that is the threshold value or more as a movement direction. Also, when speeds of the vertical and horizontal movements of the eye per unit time in the extracted image are the threshold value or more and the eye movement is determined as rotary movement, the eye movement analyzer 230 may determine the horizontal direction as a rotation direction.

The eye movement analyzer 230 may determine a vertical, horizontal, or rotary direction (right, left, up, down) and then determine a direction of an arrow to be output through the analysis result outputter 240. The eye movement analyzer 230 may determine an eye direction observed from a key frame, which corresponds to a peak where variation in movement per unit time is the greatest, as the direction of the arrow. That is, the eye movement analyzer 230 may allow a direction of a quick component moving most quickly among states of eye movement to be displayed with an arrow.

The analysis result outputter 240 may provide, together with an eye movement direction (right, left, up, down) indicating that the eye movement corresponds to the vertical, horizontal, or rotary movement, a direction of a quick component among components of the eye movement using an arrow and may express the eye movement as an animation. For example, as illustrated in FIG. 7, the analysis result outputter 240 may output, together with information indicating that directions of eye movement correspond to right and left, a direction of movement of a quick component using an arrow.

As described above, according to the present disclosure, since direct exposure of a patient's face is not required, a problem of patient information leakage can be minimized, and the present disclosure can be utilized in diagnosing dizziness by being applied to a telemedicine platform in which an eye movement is identically expressed in a virtual avatar in a metaverse.

Also, since an arrow indicating an eye direction is provided, a tester can easily identify an eye movement.

Also, when a patient has not focused on the test and proper data is not acquired, feedback is provided to the patient while the corresponding data is automatically excluded, and thus accuracy of eye movement analysis can be improved.

In addition, due to being configured using software, the present disclosure can be universally utilized when a camera with certain performance is provided.

Meanwhile, the steps of a method or algorithm described above in relation to embodiments of the present disclosure may be directly implemented by hardware, implemented by a software module executed by hardware, or implemented by a combination thereof. The software module may reside in a random access memory (RAM), a read only memory (ROM), an erasable programmable ROM (EPROM), an electrically erasable programmable ROM (EEPROM), a flash memory, a hard disk, a detachable disk, a CD-ROM, or any other computer-readable recording medium having an arbitrary form that is well known in the art to which the present disclosure pertains.

The components of the present disclosure may be implemented as a program (or application) and stored in a medium in order to be run by being combined with a computer, which is hardware. The components of the present disclosure may be executed by software programming or software elements, and likewise, an embodiment may include various algorithms implemented by a combination of data structures, processes, routines, or other programming configurations and may be implemented by a programming or scripting language such as C, C++, Java, and assembler. Functional aspects may be implemented by an algorithm executed by one or more processors.

Exemplary embodiments of a method and apparatus for analyzing eye movement according to the present disclosure have been described above, but the present disclosure is not limited thereto. Various modifications are possible within the scope of the claims, the detailed description above, and the accompanying drawings, and such modifications also belong to the present disclosure.

What is claimed is:

1. An eye movement analysis method performed in an eye movement analysis apparatus, the eye movement analysis method comprising:

(a) receiving a facial image;

(b) determining a midpoint position of an eye in the facial image and obtaining an eye image that corresponds to the eye;

(c) analyzing movement of the eye based on movement of the midpoint position in the eye image; and (d) visually displaying a direction of the movement of the eye, wherein step (c) includes:

detecting blinking of the eye in the eye image using an artificial intelligence model and classifying the blinking of the eye into an open state, a closing state, and a closed state;

extracting images classified as the open state and the closing state, among classifications of the blinking of the eye, from the eye image;

predicting a midpoint position of the closing state, among the classifications of the blinking of the eye, in the eye image by restoring a part of the eye that is covered by an eyelid;

interpolating a midpoint position of the closed state, among the classifications of the blinking of the eye, in the eye image based on a midpoint position of the closing state prior to the closed state and a midpoint position of the open state after the closed state;

detecting an eye movement consisting of a slow component and a quick component among vertical, horizontal, and rotary movements of the eye from the extracted image; and detecting an eye movement consisting of only the slow component or an eye movement consisting of only the quick component among the vertical, horizontal, and rotary movements of the eye from the extracted image, and the rotary movement is defined as a movement in which the vertical and horizontal movements of the eye simultaneously occur in the extracted image.

2. The eye movement analysis method of claim 1, wherein step (b) includes:

detecting a pupil object through image segmentation in the facial image; and searching for the midpoint position of the eye by calculating a central moment of the pupil object based on the detected pupil object.

3. The eye movement analysis method of claim 1, wherein step (d) includes providing an auditory alarm to a testee in a case in which the closed state continues for a certain amount of time or more in the eye image.

4. The eye movement analysis method of claim 1, wherein step (d) includes, in a case in which the eye movement consisting of only the slow component or the eye movement consisting of only the quick component is detected, providing a visual alarm to a tester.

5. The eye movement analysis method of claim 1, wherein step (c) includes:

selecting a frame with a peak value at which a size of a change amount of the vertical or horizontal movement of the eye per unit time in the extracted image is the largest as a key frame;

setting a speed of the slow component based on the selected key frame; and determining a component as the quick component in a case in which a speed of the component is a threshold value or more based on the speed of the slow component and determining a component as the slow component in a case in which a speed of the component is less than the threshold value.

6. The eye movement analysis method of claim 1, further comprising:

in a case in which a speed of one of the vertical and horizontal movements of the eye per unit time in the extracted image is less than a threshold value and a speed of the other movement is the threshold value or more, determining a direction of the vertical or horizontal movement having the speed that is the threshold value or more as a movement direction; and in a case in which speeds of the vertical and horizontal movements of the eye per unit time in the extracted image are the threshold value or more, determining the movement of the eye as the rotary movement and determining the horizontal direction as a rotation direction.

7. The eye movement analysis method of claim 6, further comprising:

selecting a frame with a peak value at which a size of a change amount of a movement of the eye per unit time in the extracted image is the largest as a key frame; and determining a direction of the eye that is observed from the selected key frame as a direction of an arrow.

8. The eye movement analysis method of claim 6, wherein step (d) includes:

providing, together with an eye movement direction indicating that the eye movement corresponds to the vertical, horizontal, or rotary movement, a direction of an arrow that corresponds to a direction of the quick component among the components of the eye movement; and expressing the eye movement as an animation.

9. An eye movement analysis apparatus comprising:

a facial image receiver configured to receive a facial image;

an eye image obtainer configured to obtain an eye image that corresponds to a part of an eye that determines a midpoint position of the eye in the facial image;

an eye movement analyzer configured to analyze movement of the eye based on movement of the midpoint position in the eye image; and an analysis result outputter configured to visually display a direction of the movement of the eye, wherein the eye movement analyzer is further configured to:

detect blinking of the eye in the eye image using an artificial intelligence model and classifying the blinking of the eye into an open state, a closing state, and a closed state;

extract images classified as the open state and the closing state, among classifications of the blinking of the eye, from the eye image;

predict a midpoint position of the closing state, among the classifications of the blinking of the eye, in the eye image by restoring a part of the eye that is covered by an eyelid;

interpolate a midpoint position of the closed state, among the classifications of the blinking of the eye, in the eye image based on a midpoint position of the closing state prior to the closed state and a midpoint position of the open state after the closed state;

detect an eye movement consisting of a slow component and a quick component among vertical, horizontal, and rotary movements of the eye from the extracted image; and detect an eye movement consisting of only the slow component or an eye movement consisting of only the quick component among the vertical, horizontal, and rotary movements of the eye from the extracted image, and the rotary movement is defined as a movement in which the vertical and horizontal movements of the eye simultaneously occur in the extracted image.

10. A computer program stored in a computer-readable medium, wherein, in a case in which a command of the computer program is executed, the eye movement analysis method of claim 1 is performed.

* * * * *